United States Patent [19]

Wenderoth et al.

[11] Patent Number: 5,051,447
[45] Date of Patent: Sep. 24, 1991

[54] OXIME ETHERS, THEIR PREPARATION AND FUNGICIDES CONTAINING THESE COMPOUNDS

[75] Inventors: Bernd Wenderoth, Lampertheim; Franz Schuetz, Ludwigshafen; Siegbert Brand, Weinheim; Hubert Sauter, Mannheim; Eberhard Ammermann, Ludwigshafen; Gisela Lorezn, Neustadt, all of Fed. Rep. of Germany

[73] Assignee: BASF Aktiengesellschaft, Ludwigshafen, Fed. Rep. of Germany

[21] Appl. No.: 382,418

[22] Filed: Jul. 20, 1989

[30] Foreign Application Priority Data

Aug. 12, 1988 [DE] Fed. Rep. of Germany ....... 3827361

[51] Int. Cl.$^5$ ............................................. A61K 31/235
[52] U.S. Cl. .................................... 514/534; 514/530; 514/531; 514/543; 514/544; 514/548; 560/35; 560/22; 560/9; 560/84; 560/100; 560/106; 560/117; 560/119; 560/124; 560/125; 560/154; 560/180; 560/192; 560/193
[58] Field of Search ................... 560/35, 105, 106, 22, 560/9, 154, 180, 192, 193, 117, 119, 124, 125, 100, 84; 514/535, 530, 531, 543, 544, 538, 534

[56] References Cited

U.S. PATENT DOCUMENTS 4,415,743 11/1983 Martin .................................. 560/35

FOREIGN PATENT DOCUMENTS 0253213 1/1988 European Pat. Off. ............ 514/538
0254426 1/1988 European Pat. Off. ............ 514/538

*Primary Examiner*—James H. Reamer
*Attorney, Agent, or Firm*—Oblon, Spivak, McClelland, Maier & Neustadt

[57] ABSTRACT

Oxime ethers of the general formula

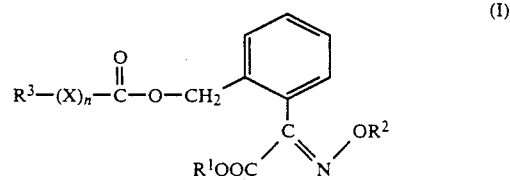

where
$R^1$ and $R^2$ are hydrogen or alkyl,
$R^3$ is hydrogen, halogen, cyano, aryl or aryloxy, the aromatic ring being unsubstituted or substituted, or $R^3$ is heteroaryl, adamantyl, fluorenyl or cycloalkyl or cycloalkenyl, these radicals being unsubstituted or substituted,
X is saturated or unsaturated $C_1$-$C_{12}$-alkylene which is unsubstituted or substituted, and
n is 0 or 1,
and fungicides containing these compounds.

6 Claims, No Drawings

OXIME ETHERS, THEIR PREPARATION AND FUNGICIDES CONTAINING THESE COMPOUNDS

The present invention relates to novel oxime ether derivatives, their preparation, fungicides containing these compounds and their use as fungicides. It is known that oxime ethers, for example 2-benzyloxyphenyl-glyoxylic acid methyl ester O-methyloxime, can be used as fungicides (EP 253 213 and 254 426). However, their fungicidal action is often inadequate.

We have found that novel fungicidal oxime ethers of the formula I

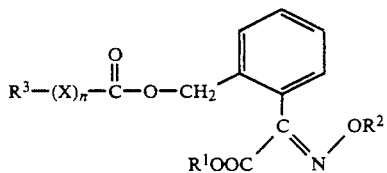

where $R^1$ and $R^2$ are each hydrogen or $C_1$-$C_5$-alkyl, $R^3$ is hydrogen, halogen, cyano, aryl or aryloxy, the aromatic ring being unsubstituted or substituted by $C_1$-$C_6$-alkyl, $C_2$-$C_4$-alkenyl, $C_1$- or $C_2$-haloalkyl, $C_1$-$C_6$-haloalkoxy, $C_1C_4$-alkoxy-$C_1C_4$-alkyl, aryl, aryl-$C_1$- or, -$C_2$-alkoxyl, aryloxy, aryloxy-$C_1$-$C_1$-alkyl, aryloxy-$C_1$-$C_4$-alkyl, haloaryloxy-$C_1$-$C_4$-alkoxy, halogen, halo-$C_1$-$C_4$-alkoxy, $C_1$-$C_4$-alkylthio, thiocyanato, cyano or nitro, or $R^3$ is hetaryl, adamantyl, fluorenyl or a $C_3$-$C_7$-cycloalkyl radical or $C_5$or $C_6$-cycloalkenyl radical, these radicals being unsubstituted or substituted by $C_1$-$C_4$-alkyl (methyl or ethyl), halogen (chlorine or bromine), $C_1$- or $C_2$-haloalkyl (trifluoromethyl, tetrabromoethyl or dichlorodibromoethyl), $C_3$- or -$C_4$-alkenyl (methylvinyl or dimethylvinyl), $C_2$-$C_4$-haloalkenyl (dichlorovinyl, dichlorobutadienyl, difluorovinyl or trifluoromethylvinyl), acetyl, methoxycarbonyl $C_3$- or -$C_4$-alkenyl (methylmethoxycarbonylviny), cyclopentylidenemethyl, halophenyl (chlorophenyl), phenyl, $C_2$- or $C_2$-alkoxyphenyl (ethoxyphenyl) or $C_1$-$C_4$-alkylphenyl (tert-butylphenyl), X is a straight-chain or branched, unsaturated or saturated $C_1$-$C_{12}$-alkylene radical which is unsubstituted or substituted by halogen or hydroxyl, and n is 0 or 1, have an excellent fungicidal action.

The radicals stated in formula I may have, for example, the following meanings:

$R^1$ and $R^2$ are identical or different and are each, for example, hydrogen or $C_1$-$C_5$-alkyl, e.g. methyl, ethyl, propyl, isopropyl, butyl or pentyl.

$R^3$ may be, for example, hydrogen, halogen (e.g. fluorine, chlorine or bromine), cyano, aryl (phenyl or naphthyl) or aryloxy (phenoxy), the aromatic ring being unsubstituted or substituted by not more than three of the following radicals: $C_1$-$C_6$-alkyl (e.g. methyl, ethyl, n-propyl, isopropyl, n-butyl, isobutyl, sec-butyl, tertbutyl, n-pentyl, isopentyl, sec-pentyl, tert-pentyl, neopentyl or hexyl), $C_2$-$C_4$-alkenyl (e.g. vinyl or allyl), $C_1$- or $C_2$-haloalkyl (e.g. difluoromethyl or trifluoromethyl), $C_1$-$C_6$-alkoxy (e.g. methoxy, ethoxy, isopropoxy or tertbutoxy), $C_1$-$C_4$-alkoxy-$C_1$-$C_4$-alkyl (e.g. methoxymethyl), aryl (e.g. phenyl), aryl-$C_1$- or -$C_2$-alkyl (e.g. benzyl), aryloxy (e.g. phenoxy), aryloxy-$C_1$-$C_4$-alkyl (e.g. phenoxymethyl or phenoxyethyl), aryloxy-$C_1$-$C_4$-alkoxy, haloaryloxy-$C_1$-$C_4$-alkoxy (e.g. phenoxymethoxy, phenoxyethoxy, phenoxypropoxy, 2-chlorophenoxyethoxy or 4-chlorophenoxyethoxy), halogen (e.g. fluorine, chlorine, bromine or iodine), halo-$C_1$-$C_4$-alkoxy (e.g. 1,1,2,2-tetrafluoroethoxy), $C_1$-$C_4$-alkylthio (e.g. methylthio), thiocyanato, cyano or nitro.

$R^3$ may furthermore be hetaryl (e.g. pyridyl, quinolyl, pyrimidinyl, furyl or pyrrolyl), the heterocyclic system being unsubstituted or monosubstituted, disubstituted or trisubstituted by aryl (phenyl), $C_1$-$C_4$-alkyl (e.g. methyl, propyl or butyl), acetyl and/or halogen (e.g. fluorine or chlorine), or $R^3$ may furthermore be $C_3$-$C_7$-cycloalkyl, $C_5$- or $C_6$-cycloalkenyl (e.g. cyclopropyl, cyclobutyl, cyclopentyl, cyclopentenyl, cyclohexyl, 1-methylcyclohexyl, cyclohexenyl or cycloheptyl), 1-adamantyl, 9-fluorenyl or a cyclopropyl radical which is monosubstituted to tetrasubstituted by $C_1$-$C_4$-alkyl (methyl or ethyl), halogen (chlorine or bromine), $C_1$- or $C_2$-haloalkyl (trifluoromethyl, tetrabromoethyl or dichlorodibromoethyl), $C_3$- or $C_4$-alkenyl (methylvinyl or dimethylvinyl), $C_2$- $C_4$-haloalkenyl (dichlorovinyl, dichlorobutadienyl, difluorovinyl or trifluoromethylvinyl), methoxycarbonyl-$C_3$-or -$C_4$-alkenyl (methylmethoxycarbonylvinyl), cyclopentylidenemethyl, phenyl, halophenyl (chlorophenyl or bromophenyl), $C_1$- or $C_2$-alkoxyphenyl (methoxyphenyl or ethoxyphenyl) or $C_1$-$C_4$-alkylphenyl (tert-butylphenyl), for example:

2,2-dimethyl-3-(2',2'-dimethylvinyl)-cyclopropyl (A1)
2,2-dimethyl-3-(2',2'-dichlorovinyl)-cyclopropyl (A2)
2,2-dimethyl-3-(2',2'-dibromovinyl)-cyclopropyl (A3)
2,2-dimethyl-3-(2'-trifluoromethyl-2'-chlorovinyl)-cyclopropyl (A4)
2,2-dichloro-3,3-dimethylcyclopropyl (A5)
2,2,3,3-tetramethylcyclopropyl (A6)
2,2-dimethyl-3-(2',2'-difluorovinyl)-cyclopropyl (A7)
2,2-dimethyl-3-(2'-trifluoromethyl-2'-fluorovinyl)-cyclopropyl (A8)
2,2-dimethyl-3-(2'-methyl-2'-methoxycarbonylvinyl)-cyclopropyl (A9)
2,2-dimethyl-3-(4',4'-dichlorobutadienyl)-cyclopropyl (A10)
2,2-dimethyl-3-(1'-bromo-2',2',2'-tribromoethyl)-cyclopropyl (A11)
2,2-dimethyl-3-(1'-bromo-2',2'-dichloro-2'-bromoethyl)-cyclopropyl (A12)
1-(2',4'-dichlorophenyl)-cyclopropyl (A13)
1-(4'-chlorophenyl)-cyclopropyl (A14)
1-(4'-ethoxyphenyl)-2,2-dichlorocyclopropyl (A15)
2,2-dimethyl-3-(4'-tert-butylphenyl)-cyclopropyl (A16)
1-methyl-2,2-dichlorocyclopropyl (A17).

X may be, for example, a straight-chain $C_1$-$C_{12}$-alkylene radical (eg. methylene, ethylene, propylene, butylene, pentylene, hexylene or heptylene), a branched $C_1$-$C_{12}$-alkylene radical (eg. methylmethylene, dimethylmethylene, ethylmethylene, n-propylmethylene, isopropylmethylene, methylethylene, methylpropylene, dimethylpropylene, ethylpropylene, methylbutylene, dimethylbutylene, ethylbutylene, n-propylbutylene, isopropylbutylene, methylpentylene, dimethylpentylene, trimethylpentylene, methylhexylene, dimethylhexylene, trimethylhexylene, ethylhexylene, n-propylhexylene, isopropylhexylene or methylheptylene), a $C_2$-$C_8$-alkenylene radical (eg. vinylene, allylene, methylallylene, butenylene or methylbutenylene), a halogen-substituted $C_1$-$C_{12}$-alkylene radical (eg. chloromethylene, dichloromethylene, fluoromethylene, difluoromethylene, bromomethylene, dibromomethylene, chloroethylene, fluoroethylene, bromoethylene, fluoropropylene, chloropropylene, bromopropylene, fluorobutylene, chlorobutylene or bromobutylene), a halogen-substituted $C_2$-$C_4$-alkenylene radical (eg. chlorovinylene or dichlorovinylene) or a hydroxyl-substituted $C_1$-$C_8$-alkylene radical (eg. hydroxymethylene or hydroxyethylene).

Where n is 0, $X_n$ is a single bond.

Because of the C=N double bond, the novel compounds of the formula I may be obtained in their preparation as E/Z isomer mixtures, which can be separated into the individual components in a conventional manner, for example by crystallization or chromatography. Both the individual isomeric compounds and their mixtures form the subject of the present invention and can be used as fungicides.

The novel compounds of the formula I can be prepared, for example, by reacting an ortho-substituted benzyl bromide of the general formula III, where $R^1$ and $R^2$ have the abovementioned meanings, with an alkali metal, alkaline earth metal or ammonium salt of a carboxylic acid of the formula II, where $R^3$, X and n have the abovementioned meanings, in a solvent or diluent and with or without the addition of a catalyst to give the novel compounds.

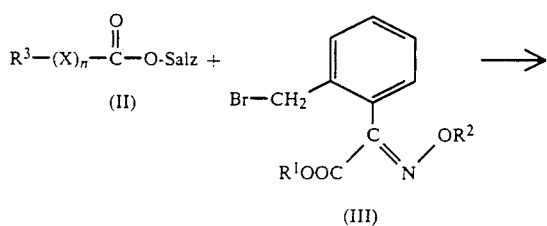

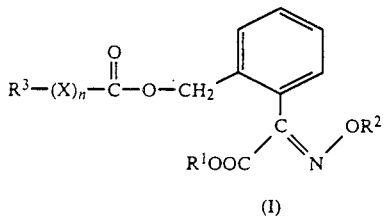

The preparation of carboxylic esters from alkyl halides and carboxylates is known (cf. for example Synthesis 1975, 805).

Suitable solvents or diluents for the reaction of II with III are acetone, acetonitrile, dimethyl sulfoxide, dioxane, dimethylformamide, N-methylpyrrolidone, N,N'-dimethylpropyleneurea and pyridine.

It may also be advantageous to add a catalyst, for example potassium iodide or tetramethylethylenediamine, in an amount of from 0.01 to 10% by weight, based on the compound III, to the reaction mixture.

The corresponding reactions can also be carried out in a two-phase system (for example carbon tetrachloride/water). Examples of suitable phase transfer catalysts are trioctylpropylammonium chloride and cetyltrimethylammonium chloride (cf. Synthesis 1974, 867).

The carboxylates of the formula II are known. They can be prepared from the corresponding carboxylic acids using bases (eg. potassium hydroxide) in an inert solvent (eg. ethanol).

The ortho-substituted benzyl bromides of the formula III can be prepared by reacting an α-ketocarboxylic ester of the formula IV, known from the literature (cf. for example J. M. Photis, Tetrahedron Lett. 1980, 3539),

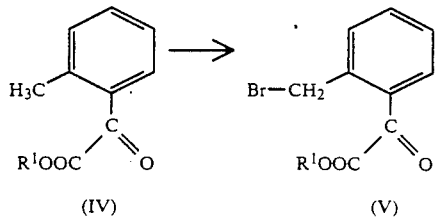

with bromine in a solvent, for example tetrachloromethane, if necessary with exposure to a light source (for example an Hg vapor lamp, 300 W) or with N-bromosuccinimide (Horner and Winkelmann, Angew. Chem. 71 (1959), 349), to give the α-ketocarboxylic esters of the general formula V, where $R^1$ has the abovementioned meanings.

The bromides of the formula III can be prepared by reacting an α-ketocarboxylic ester of the formula V a) with an O-substituted hydroxylamine of the formula $H_2N-OR^2$, where $R^2$ has the abovementioned meanings, or b) with hydroxylamine to give the corresponding oxime and then reacting the latter with an alkyl halide of the formula $R^2-X$, where $R^2$ has the abovementioned meanings and X is a halogen atom (F, Cl, Br or I), or with a dialkyl sulfate.

The novel compounds of the formula I can also be prepared, for example, by reacting a novel α-ketocarboxylic ester of the formula VI

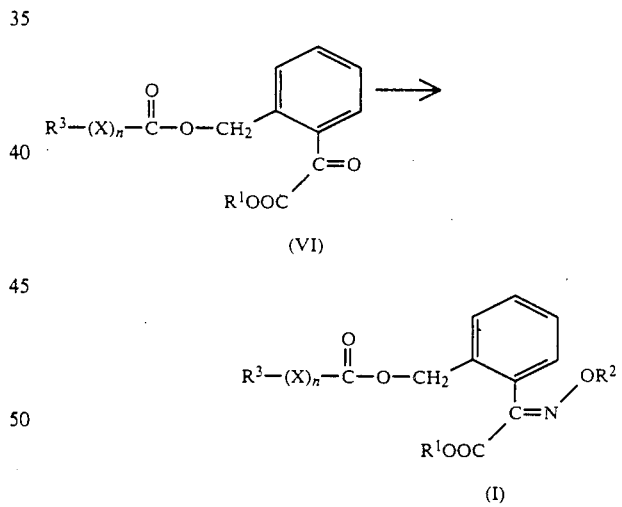

a) with an O-substituted hydroxylamine of the formula $H_2NOR^2$, where $R^2$ has the abovementioned meanings, or b) with hydroxylamine to give the corresponding oxime and then reacting the latter with an alkyl halide of the formula $R^2-X$, where $R^2$ has the abovementioned meanings and X is a halogen atom (F, Cl, Br or I), or with a dialkyl sulfate.

The novel α-ketocarboxylic esters of the general formula VI are useful intermediates. They can be prepared, for example, by reacting the abovementioned compound of the formula V with an alkali metal, alkaline earth metal or ammonium salt of a carboxylic acid of the formula II, where $R^3$, $R^1$, X and n have the abovementioned meanings, in a solvent or diluent and with or without the addition of a catalyst to give the novel compounds of the formula VI:

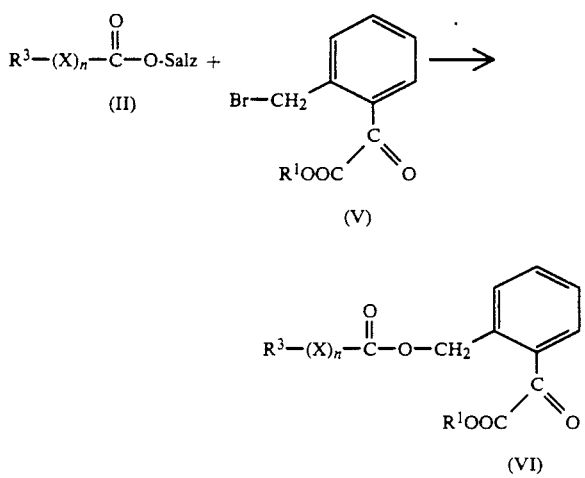

The preparation of carboxylic esters from alkyl halides and carboxylates is known (cf. for example Synthesis 1975, 805).

Suitable solvents or diluents for the reaction of II with V are acetone, acetonitrile, dimethyl sulfoxide, dioxane, dimethylformamide, N-methylpyrrolidone, N,N'-dimethylpropylene urea and pyridine.

It may furthermore be advantageous to add a catalyst, for example potassium iodide or tetramethylethylenediamine in an amount of from 0.01 to 10% by weight, based on compound V, to the reaction mixture.

The corresponding reactions can also be carried out in a two-phase system (for example carbon tetrachloride/water). Examples of suitable phase transfer catalysts are trioctylpropylammonium chloride and cetyltrimethylammonium chloride (cf. Synthesis 1974, 867).

The Examples which follow illustrate the preparation of the novel compounds of the formula I.

METHOD 1

Preparation of methyl 2-(bromomethyl)-phenylglyoxylate 5.34 g (30 millimoles) of methyl 2-methylphenylglyoxylate and 5.34 g (30 millimoles) of N-bromosuccinimide in 1,000 ml of tetrachloromethane are exposed to a 300 W Hg vapor lamp for one hour. Thereafter, the organic phase is washed once with water and three times with sodium bicarbonate solution and dried over sodium sulfate/sodium carbonate. It is evaporated down and the crude product is then chromatographed over silica gel using 9:1 methyl tert-butyl ether/n-hexane. 3.8 g (49%) of the abovementioned compound is obtained as a yellow oil.

$^1$H-NMR (CDCl$_3$): δ = 3.97 (s, 3H), 4.90 (s, 2H), 7.4–7.8 (m, 4H).

IR (film): 2955, 1740, 1689, 1435, 1318, 1207, 999, cm$^{-1}$.

METHOD 2

Preparation of methyl 2-(α-methylcyclopropylcarboxymethylene)-phenylglyoxylate 13.8 g (0.1 mole) of the potassium salt of α-methylcyclopropanecarboxylic acid, 21.1 g (0.082 mole) of methyl 2-(bromomethyl)-phenylglyoxylate and 0.3 g of potassium iodide are dissolved in 300 ml of N-methylpyrrolidone. The mixture is stirred for 15 hours at 23° C., poured onto 300 ml of ice water and extracted with 3×200 ml of methyl tert-butyl ether. The organic phases are washed with water, dried with sodium sulfate and evaporated down. The abovementioned compound is obtained in quantitative yield.

$^1$H-NMR (CDCl$_3$): δ = 0.70 (m, 2H), 1.27 (m, 2H), 1.35 (s, 3H), 3.96 (s, 3H), 5.46 (s, 2H), 7.4–7.8 (m, 4H).

METHOD 3

Preparation of 2-(bromomethyl)-phenylglyoxylic acid methyl ester O-methyloxime 21.4 g (0.133 mole) of bromine are added to 27.5 g (0.133 mole) of 2-methylphenylglyoxylic acid methyl ester O-methyloxime dissolved in 400 ml of tetrachloromethane, while stirring. Thereafter, the mixture is refluxed for four hours with exposure to a 300 W Hg vapor lamp. It is then evaporated down, the residue is taken up in ethyl acetate/water and the solution is washed with H$_2$O, dried with sodium sulfate and evaporated down. The crude product is purified by chromatography over silica gel using 9:1 cyclohexane/ethyl acetate. 17.4 g (46%) of the abovementioned compound is obtained as an oil.

$^1$H-NMR (CDCl$_3$): δ = 3.88 (s, 3H), 4.08 (s, 3H), 4.33 (s, 2H), 7.12–7.52 (m, 4H).

EXAMPLE 1

2-(α-Methylcyclopropylcarboxymethylene)-phenylglyoxylic acid methyl ester O-methyloxime (Compound No. 316)

5.1 g (37 millimoles) of potassium α-methylcyclopropylcarboxylate together with a pinch of potassium iodide in 125 ml of absolute N,N-dimethylformamide are initially taken. 8.9 g (31 millimoles) of 2-(bromomethyl)-phenylglyoxylic acid methyl ester O-methyloxime (dissolved in a little N,N-dimethylformamide) are added dropwise and the mixture is stirred for 5 hours at 100° C. It is then filtered under suction and the filtrate is evaporated down. The residue is taken up in ether and the solution is washed with H$_2$O, dried over sodium sulfate and evaporated down. The residue is chromatographed over silica gel using 9:1 cyclohexane/ethyl acetate, and 2.7 g (28.5%) of the abovementioned compound are obtained as white crystals of melting point 94°–96° C.

$^1$H-NMR (CDCl$_3$): δ = 0.65 (m, 2H), 1.20 (m, 2H), 1.30 (s, 3H), 3.85 (s, 3H), 4.05 (s, 3H), 4.95 (s, 2H), 7.18 (m, 1H), 7.40 (m, 3H).

The compounds listed in the Table below can be prepared in a similar manner.

TABLE 1

$$R^3-(X)_n-\overset{O}{\overset{\|}{C}}-O-CH_2-\underset{\underset{C}{\bigcirc}}{}-\underset{R^1OOC}{\overset{OR^2}{\underset{\|}{C}=N}}$$

| No. | R³ | (X)ₙ | R² | R¹ | mp (°C.) | IR (cm⁻¹) |
|---|---|---|---|---|---|---|
| 1 | H | —CH₂— | CH₃ | CH₃ | | |
| 2 | H | —CH₂—CH₂— | CH₃ | CH₃ | | |
| 3 | H | —CH₂—CH(CH₃)— | CH₃ | CH₃ | | |
| 4 | H | —CH₂—C(CH₃)₂— | CH₃ | CH₃ | 56–59 | 2980, 1728, 1281, 1221, 1159, 1069, 1020, 959 |
| 5 | H | —CH=CH— | CH₃ | CH₃ | | |
| 6 | H | —CH=C(CH₃)— | CH₃ | CH₃ | | |
| 7 | H | —C≡C— | CH₃ | CH₃ | | |
| 8 | H | —CH₂—CH₂—CH₂— | CH₃ | CH₃ | | |
| 9 | H | —CH₂—CH(CH₃)—CH₂— | CH₃ | CH₃ | | |
| 10 | H | —CH₂—CH(CH₃)—CH₂— | CH₃ | CH₃ | | |
| 11 | H | —CH₂—CH₂—C(CH₃)₂— | CH₃ | CH₃ | 44–47 | 2980, 1738, 1719, 1297, 1155, 1067, 1008, 772 |
| 12 | H | —CH₂—C(CH₃)₂—CH₂— | CH₃ | CH₃ | | |
| 13 | H | —CH₂—C(CH₃)₂—C(C₂H₅)₂— | CH₃ | CH₃ | | |
| 14 | H | —CH=CH—CH=CH— | CH₃ | CH₃ | | |
| 15 | H | —CH₂—CH=CH— | CH₃ | CH₃ | | |
| 16 | H | —CH₂—C(CH₃)=CH— | CH₃ | CH₃ | | |
| 17 | H | —CH₂—CH=C(CH₃)— | CH₃ | CH₃ | | |
| 18 | H | —(CH₂)₄— | CH₃ | CH₃ | | |
| 19 | H | —CH₂—CH₂—CH₂—CH(CH₃)— | CH₃ | CH₃ | | |
| 20 | H | —CH₂—CH(CH₃)—CH₂—CH₂— | CH₃ | CH₃ | | |
| 21 | H | —(CH₂)₂—C(CH₃)₂— | CH₃ | CH₃ | | |
| 22 | H | —(CH₂)₃—CH(C₂H₅)— | CH₃ | CH₃ | | |
| 23 | H | —(CH₂)₃—CH(n-C₃H₇)— | CH₃ | CH₃ | | |
| 24 | H | —CH₂—CH=CH—CH₂— | CH₃ | CH₃ | | |
| 25 | H | —CH₂—C(CH₃)=CH—CH₂— | CH₃ | CH₃ | | |
| 26 | H | —(CH₂)₅— | CH₃ | CH₃ | oil | 2958, 1732, 1220, 1069, 1020 |
| 27 | H | —(CH₂)₄—CH(CH₃)— | CH₃ | CH₃ | | |
| 28 | H | —(CH₂)₄—CH(C₂H₅)— | CH₃ | CH₃ | | |
| 29 | H | —CH₂—CH=CH(CH₃)—CH₂— | CH₃ | CH₃ | | |
| 30 | H | —CH₂—CH=CH—CH=CH— | CH₃ | CH₃ | | |
| 31 | H | —CH₂—C(CH₃)=CH—CH=CH— | CH₃ | CH₃ | | |
| 32 | H | —(CH₂)₆— | CH₃ | CH₃ | oil | 2935, 1737, 1221, 1069, 1020 |
| 33 | H | —(CH₂)₅—CH(CH₃)— | CH₃ | CH₃ | | |
| 34 | H | —(CH₂)₄—CH(CH₃)—CH₂— | CH₃ | CH₃ | | |
| 35 | H | —(CH₂)₅—CH(n-C₃H₇)— | CH₃ | CH₃ | | |
| 36 | H | —(CH₂)₇— | CH₃ | CH₃ | | |

TABLE 1-continued

Structure:

$$R^3-(X)_n-\overset{O}{\underset{}{C}}-O-CH_2-\underset{}{\overset{}{C_6H_4}}-\overset{OR^2}{\underset{R^1OOC}{C=N}}$$

| No. | R³ | (X)ₙ | R² | R¹ | mp (°C.) | IR (cm⁻¹) |
|---|---|---|---|---|---|---|
| 37 | H | —(CH₂)₆—CH(CH₃)— | CH₃ | CH₃ | | |
| 38 | H | —(CH₂)₅—CH(CH₃)—CH₂— | CH₃ | CH₃ | | |
| 39 | H | —(CH₂)₆—C(CH₃)₂— | CH₃ | CH₃ | | |
| 40 | H | —(CH₂)₈— | CH₃ | CH₃ | | |
| 41 | H | —(CH₂)₉— | CH₃ | CH₃ | | |
| 42 | H | —(CH₂)₁₀— | CH₃ | CH₃ | | |
| 43 | H | —CHCl— | CH₃ | CH₃ | | |
| 44 | Cl | —CCl₂— | CH₃ | CH₃ | | |
| 45 | H | —CCl₂— | CH₃ | CH₃ | | |
| 46 | H | —CHBr— | CH₃ | CH₃ | | |
| 47 | Br | —CBr₂— | CH₃ | CH₃ | | |
| 48 | H | —CBr₂— | CH₃ | CH₃ | | |
| 49 | H | —CHF— | CH₃ | CH₃ | | |
| 50 | F | —CF₂— | CH₃ | CH₃ | | |
| 51 | H | —CF₂— | CH₃ | CH₃ | | |
| 52 | H | —CH=CCl— | CH₃ | CH₃ | | |
| 53 | Cl | —CCl=CCl— | CH₃ | CH₃ | | |
| 54 | H | —C(CH₃)₂— | CH₃ | CH₃ | | |
| 55 | H | —C(CH₃)₂— | CH₃ | CH₃ | | |
| 56 | H | —CHCl—CH(CH₃)— | CH₃ | CH₃ | | |
| 57 | H | —CHCl—C(CH₃)₂— | CH₃ | CH₃ | | |
| 58 | H | —CHBr—CH(CH₃)— | CH₃ | CH₃ | | |
| 59 | Br | —C(C₂H₅)₂— | CH₃ | CH₃ | | |
| 60 | H | —CH(OH)— | CH₃ | CH₃ | | |
| 61 | H | —CH₂—CH(OH)— | CH₃ | CH₃ | | |
| 62 | H | —CH₂—CH₂—CH(OH)— | CH₃ | CH₃ | | |
| 63 | H | —CH₂—CH(OH)—CH₂— | CH₃ | CH₃ | | |
| 64 | H | —CH(OH)—CH₂— | CH₃ | CH₃ | | |
| 65 | H | —CH(OH)—C(CH₃)₂— | CH₃ | CH₃ | | |
| 66 | H | —CH₂—C(OH)(CH₃)— | CH₃ | CH₃ | | |
| 67 | H | —CH₂—CH(CH₃)—CH(OH)— | CH₃ | CH₃ | | |
| 68 | H | —CH=CH—CH(OH)— | CH₃ | CH₃ | | |
| 69 | H | —CH=CH—CH₂—CH(OH)— | CH₃ | CH₃ | | 68–70 | 2950, 1729, 1398, 1222, 1167, 1069, 1019 |
| 70 | CN | —CH₂— | CH₃ | CH₃ | | |
| 71 | cyclopropyl | — | CH₃ | CH₃ | | |
| 72 | cyclobutyl | — | CH₃ | CH₃ | | |
| 73 | cyclopentyl | — | CH₃ | CH₃ | | |
| 74 | cyclohexyl | — | CH₃ | CH₃ | | |
| 75 | adamantyl | — | CH₃ | CH₃ | | |
| 76 | 9-fluorenyl | — | CH₃ | CH₃ | | |

TABLE 1-continued $$R^3-(X)_n-\overset{O}{\overset{\|}{C}}-O-CH_2-\underset{R^1OOC}{\underset{|}{C}}=N-OR^2$$ (on phenyl ring)

| No. | R³ | (X)ₙ | R² | R¹ | mp (°C.) | IR (cm⁻¹) |
|---|---|---|---|---|---|---|
| 77 | cyclopentyl | —CH₂— | CH₃ | CH₃ | | |
| 78. | 3-cyclopentenyl | —CH₂— | CH₃ | CH₃ | | |
| 79 | cyclohexyl | —CH₂— | CH₃ | CH₃ | | |
| 80 | cyclopentyl | —CH₂—CH₂— | CH₃ | CH₃ | | |
| 81 | cyclohexyl | —CH₂—CH₂— | CH₃ | CH₃ | | |
| 82 | cyclohexyl | —(CH₂)₃— | CH₃ | CH₃ | | |
| 83 | C₆H₅ (= phenyl) | — | CH₃ | CH₃ | | |
| 84 | 2-CH₃—C₆H₄ | — | CH₃ | CH₃ | | |
| 85 | 3-CH₃—C₆H₄ | — | CH₃ | CH₃ | | |
| 86 | 4-CH₃—C₆H₄ | — | CH₃ | CH₃ | | |
| 87 | 2,3-(CH₃)₂—C₆H₃ | — | CH₃ | CH₃ | | |
| 88 | 2,4-(CH₃)₂—C₆H₃ | — | CH₃ | CH₃ | | |
| 89 | 2,6-(CH₃)₂—C₆H₃ | — | CH₃ | CH₃ | 84–86 | 2960, 1726, 1261, 1245, 1069, 1014, 784 |
| 90 | 3,4-(CH₃)₂—C₆H₃ | — | CH₃ | CH₃ | | |
| 91 | 3,5-(CH₃)₂—C₆H₃ | — | CH₃ | CH₃ | | |
| 92 | 2,4,6-(CH₃)₃—C₆H₂ | — | CH₃ | CH₃ | oil | 2950, 1727, 1437, 1262, 1071, 1019 |
| 93 | 4-t-C₄H₉—C₆H₄ | — | CH₃ | CH₃ | | |
| 94 | 2-C₆H₅—C₆H₄ | — | CH₃ | CH₃ | | |
| 95 | 4-C₆H₅—C₆H₄ | — | CH₃ | CH₃ | | |
| 96 | 2-benzyl-C₆H₄ | — | CH₃ | CH₃ | | |
| 97 | 4-benzyl-C₆H₄ | — | CH₃ | CH₃ | | |
| 98 | 2-Cl—C₆H₄ | — | CH₃ | CH₃ | | |
| 99 | 3-Cl—C₆H₄ | — | CH₃ | CH₃ | | |
| 100 | 4-Cl—C₆H₄ | — | CH₃ | CH₃ | | |
| 101 | 2,4-Cl₂—C₆H₃ | — | CH₃ | CH₃ | | |
| 102 | 2,5-Cl₂—C₆H₃ | — | CH₃ | CH₃ | | |
| 103 | 2,6-Cl₂—C₆H₃ | — | CH₃ | CH₃ | 73–75 | 2950, 1738, 1433, 1270, 1142, 1069, 1019 |
| 104 | 3,4-Cl₂—C₆H₃ | — | CH₃ | CH₃ | | |
| 105 | 3,5-Cl₂—C₆H₃ | — | CH₃ | CH₃ | | |
| 106 | 2,4,5-Cl₃—C₆H₂ | — | CH₃ | CH₃ | | |
| 107 | 2,3,4,5,6-Cl₅—C₆ | — | CH₃ | CH₃ | | |
| 108 | 2-F,4-Cl—C₆H₃ | — | CH₃ | CH₃ | | |
| 109 | 2-F—C₆H₄ | — | CH₃ | CH₃ | | |
| 110 | 3-F—C₆H₄ | — | CH₃ | CH₃ | | |
| 111 | 4-F—C₆H₄ | — | CH₃ | CH₃ | | |
| 112 | 2,4-F₂—C₆H₃ | — | CH₃ | CH₃ | | |
| 113 | 2,6-F₂—C₆H₃ | — | CH₃ | CH₃ | oil | 2950, 1734, 1625, |

TABLE 1-continued structure: R³—(X)ₙ—C(=O)—O—CH₂— attached to benzene ring with C(=N—OR²)—COOR¹

| No. | R³ | (X)ₙ | R² | R¹ | mp (°C.) | IR (cm⁻¹) |
|---|---|---|---|---|---|---|
| 114 | 2,3,4,5,6-F₅—C₆ | — | CH₃ | CH₃ | | |
| 115 | 2-CF₃—C₆H₄ | — | CH₃ | CH₃ | | |
| 116 | 3-CF₃—C₆H₄ | — | CH₃ | CH₃ | | |
| 117 | 4-CF₃—C₆H₄ | — | CH₃ | CH₃ | | |
| 118 | 2-OCH₃—C₆H₄ | — | CH₃ | CH₃ | | |
| 119 | 3-OCH₃—C₆H₄ | — | CH₃ | CH₃ | | |
| 120 | 4-OCH₃—C₆H₄ | — | CH₃ | CH₃ | | |
| 121 | 2-phenoxy-C₆H₄ | — | CH₃ | CH₃ | | |
| 122 | 3-phenoxy-C₆H₄ | — | CH₃ | CH₃ | | |
| 123 | 4-phenoxy-C₆H₄ | — | CH₃ | CH₃ | | 1470, 1287, 1263, 1069, 1016 |
| 124 | 4-ethoxy-C₆H₄ | — | CH₃ | CH₃ | | |
| 125 | 2-phenoxyethoxy-C₆H₄ | — | CH₃ | CH₃ | | |
| 126 | 2-(2'-Cl-phenoxyethoxy)-C₆H₄ | — | CH₃ | CH₃ | | |
| 127 | 2-(3'-Cl-phenoxyethoxy)-C₆H₄ | — | CH₃ | CH₃ | | |
| 128 | 2-(4'-Cl-phenoxyethoxy)-C₆H₄ | — | CH₃ | CH₃ | | |
| 129 | 3-phenoxyethoxy-C₆H₄ | — | CH₃ | CH₃ | | |
| 130 | 3-(4'-Cl-phenoxyethoxy)-C₆H₄ | — | CH₃ | CH₃ | | |
| 131 | 4-phenoxyethoxy-C₆H₄ | — | CH₃ | CH₃ | | |
| 132 | 2-phenoxypropoxy-C₆H₄ | — | CH₃ | CH₃ | | |
| 133 | 3-phenoxypropoxy-C₆H₄ | — | CH₃ | CH₃ | | |
| 134 | 4-phenoxypropoxy-C₆H₄ | — | CH₃ | CH₃ | | |
| 135 | C₆H₅ | —CH₂— | CH₃ | CH₃ | | |
| 136 | 2-CH₃—C₆H₄ | —CH₂— | CH₃ | CH₃ | | |
| 137 | C₆H₅ | —CH(CH₃)— | CH₃ | CH₃ | | |
| 138 | 4-phenyl-C₆H₄ | —CH₂— | CH₃ | CH₃ | | |
| 139 | 2-F—C₆H₄ | —CH₂— | CH₃ | CH₃ | | |
| 140 | 3-F—C₆H₄ | —CH₂— | CH₃ | CH₃ | | |
| 141 | 4-F—C₆H₄ | —CH₂— | CH₃ | CH₃ | | |
| 142 | 2-Cl—C₆H₄ | —CH₂— | CH₃ | CH₃ | | |
| 143 | 3-Cl—C₆H₄ | —CH₂— | CH₃ | CH₃ | | |
| 144 | 4-Cl—C₆H₄ | —CH₂— | CH₃ | CH₃ | oil | 2950, 1737, 1492, 1231, 1221, 1070, 1016 |
| 145 | 2,4-Cl₂—C₆H₃ | —CH₂— | CH₃ | CH₃ | | |
| 146 | 2,6-Cl₂—C₆H₃ | —CH₂— | CH₃ | CH₃ | | |
| 147 | 2-Cl,4-F—C₆H₃ | —CH₂— | CH₃ | CH₃ | | |
| 148 | 2-ethoxy-C₆H₄ | —CH₂— | CH₃ | CH₃ | | |
| 149 | 4-ethoxy-C₆H₄ | —CH₂— | CH₃ | CH₃ | | |
| 150 | 2-OCH₃—C₆H₄ | —CH₂— | CH₃ | CH₃ | | |
| 151 | 4-OCH₃—C₆H₄ | —CH₂— | CH₃ | CH₃ | | |

TABLE 1-continued $$R^3-(X)_n-\overset{O}{\underset{}{C}}-O-CH_2 \text{ (phenyl) } \overset{OR^2}{\underset{R^1OOC}{C=N}}$$

| No. | R³ | (X)n | R² | R¹ | mp (°C.) | IR (cm⁻¹) |
|-----|----|----|----|----|----|----|
| 152 | 4-t-C₄H₉—C₆H₄ | —CH₂— | CH₃ | CH₃ | | |
| 153 | C₆H₅ | —CH(iso-C₃H₇)— | CH₃ | CH₃ | | |
| 154 | 4-Cl-C₆H₄ | —CH(iso-C₃H₇)— | CH₃ | CH₃ | | |
| 155 | 4-F—C₆H₄ | —CH(iso-C₃H₇)— | CH₃ | CH₃ | | |
| 156 | 4-OCF₂H—C₆H₄ | —CH(iso-C₃H₇)— | CH₃ | CH₃ | | |
| 157 | C₆H₅ | —CH(OH)— | CH₃ | CH₃ | | |
| 158 | 2-OCH₃—C₆H₄ | —CH(OH)— | CH₃ | CH₃ | | |
| 159 | 3-OCH₃—C₆H₄ | —CH(OH)— | CH₃ | CH₃ | | |
| 160 | 4-OCH₃—C₆H₄ | —CH(OH)— | CH₃ | CH₃ | | |
| 161 | 4-Cl—C₆H₄ | —CH(OH)— | CH₃ | CH₃ | | |
| 162 | C₆H₅ | —CH(CH₂OH)— | CH₃ | CH₃ | | |
| 163 | C₆H₅ | —CH₂—CH₂— | CH₃ | CH₃ | | |
| 164 | C₆H₅ | —CH(CH₃)—CH₂— | CH₃ | CH₃ | | |
| 165 | C₆H₅ | —CH₂—CH(CH₃)— | CH₃ | CH₃ | | |
| 166 | C₆H₅ | —CH(CH₃)—CH(CH₃)— | CH₃ | CH₃ | | |
| 167 | C₆H₅ | —CH(C₆H₅)—CH₂— | CH₃ | CH₃ | | |
| 168 | 4-t-C₄H₉—C₆H₄ | —CH₂—CH₂— | CH₃ | CH₃ | | |
| 169 | 4-t-C₄H₉—C₆H₄ | —CH₂—CH(CH₃)— | CH₃ | CH₃ | | |
| 170 | 2-Cl—C₆H₄ | —CH₂—CH₂— | CH₃ | CH₃ | | |
| 171 | 3-Cl—C₆H₄ | —CH₂—CH₂— | CH₃ | CH₃ | | |
| 172 | 4-Cl—C₆H₄ | —CH₂—CH₂— | CH₃ | CH₃ | | |
| 173 | 2-F—C₆H₄ | —CH₂—CH₂— | CH₃ | CH₃ | | |
| 174 | 3-F—C₆H₄ | —CH₂—CH₂— | CH₃ | CH₃ | | |
| 175 | 4-F—C₆H₄ | —CH₂—CH₂— | CH₃ | CH₃ | | |
| 176 | 2-OCH₃—C₆H₄ | —CH₂—CH₂— | CH₃ | CH₃ | | |
| 177 | 4-OCH₃—C₆H₄ | —CH₂—CH₂— | CH₃ | CH₃ | | |
| 178 | C₆H₅ | —CH=CH— | CH₃ | CH₃ | | |
| 179 | 2-Cl—C₆H₄ | —CH=CH— | CH₃ | CH₃ | | |
| 180 | 3-Cl—C₆H₄ | —CH=CH— | CH₃ | CH₃ | | |
| 181 | 4-Cl—C₆H₄ | —CH=CH— | CH₃ | CH₃ | | |
| 182 | 2,6-Cl₂—C₆H₃ | —CH=CH— | CH₃ | CH₃ | | |
| 183 | 2,4-Cl₂—C₆H₃ | —CH=CH— | CH₃ | CH₃ | | |
| 184 | 2-F—C₆H₄ | —CH=CH— | CH₃ | CH₃ | | |
| 185 | 3-F—C₆H₄ | —CH=CH— | CH₃ | CH₃ | | |
| 186 | 4-F—C₆H₄ | —CH=CH— | CH₃ | CH₃ | | |
| 187 | 2-CF₃—C₆H₄ | —CH=CH— | CH₃ | CH₃ | | |
| 188 | 4-CF₃—C₆H₄ | —CH=CH— | CH₃ | CH₃ | | |
| 189 | 4-CH₃—C₆H₄ | —CH=CH— | CH₃ | CH₃ | | |
| 190 | 4-CH₃—C₆H₄ | —CH=CH— | CH₃ | CH₃ | | |
| 191 | 4-i-C₃H₇—C₆H₄ | —CH=CH— | CH₃ | CH₃ | | |
| 192 | 4-t-C₄H₉—C₆H₄ | —CH=CH— | CH₃ | CH₃ | | |
| 193 | 2-OCH₃—C₆H₄ | —CH=CH— | CH₃ | CH₃ | | |

TABLE 1-continued

Structure:

$$R^3-(X)_n-\overset{O}{\underset{}{C}}-O-CH_2-\text{[phenyl]}-\underset{R^1OOC}{\overset{OR^2}{C=N}}$$

| No. | R³ | (X)ₙ | R² | R¹ | mp (°C.) | IR (cm⁻¹) |
|---|---|---|---|---|---|---|
| 194 | 3-OCH₃—C₆H₄ | —CH=CH— | CH₃ | CH₃ | | |
| 195 | 4-OCH₃—C₆H₄ | —CH=CH— | CH₃ | CH₃ | | |
| 196 | 2-phenoxy-C₆H₄ | —CH=CH— | CH₃ | CH₃ | | |
| 197 | 3-phenoxy-C₆H₄ | —CH=CH— | CH₃ | CH₃ | | |
| 198 | 4-phenoxy-C₆H₄ | —CH=CH— | CH₃ | CH₃ | | |
| 199 | C₆H₅ | —(CH₂)₃— | CH₃ | CH₃ | | |
| 200 | C₆H₅ | —CH(CH₃)—CH₂—CH₂— | CH₃ | CH₃ | | |
| 201 | C₆H₅ | —CH₂—CH(CH₃)—CH₂— | CH₃ | CH₃ | | |
| 202 | C₆H₅ | —CH₂—CH₂—CH(CH₃) | CH₃ | CH₃ | | |
| 203 | 2-Cl—C₆H₄ | —(CH₂)₃— | CH₃ | CH₃ | | |
| 204 | 4-Cl—C₆H₄ | —(CH₂)₃— | CH₃ | CH₃ | | |
| 205 | 2-OCH₃—C₆H₄ | —(CH₂)₃— | CH₃ | CH₃ | | |
| 206 | 4-OCH₃—C₆H₄ | —(CH₂)₃— | CH₃ | CH₃ | | |
| 207 | 4-t-C₄H₉—C₆H₄ | —(CH₂)₃— | CH₃ | CH₃ | | |
| 208 | C₆H₅ | —CH=CH—CH₂— | CH₃ | CH₃ | | |
| 209 | C₆H₅ | —(CH₂)₄— | CH₃ | CH₃ | | |
| 210 | 2-Cl—C₆H₄ | —(CH₂)₄— | CH₃ | CH₃ | | |
| 211 | 4-Cl—C₆H₄ | —(CH₂)₄— | CH₃ | CH₃ | | |
| 212 | 2-OCH₃—C₆H₄ | —(CH₂)₄— | CH₃ | CH₃ | | |
| 213 | 4-OCH₃—C₆H₄ | —(CH₂)₄— | CH₃ | CH₃ | | |
| 214 | 4-CF₃—C₆H₄ | —(CH₂)₄— | CH₃ | CH₃ | | |
| 215 | 2-CH₃—C₆H₄ | —(CH₂)₄— | CH₃ | CH₃ | | |
| 216 | 4-CH₃—C₆H₄ | —(CH₂)₄— | CH₃ | CH₃ | | |
| 217 | C₆H₅ | —CH₂—CH₂—CH(CH₃)—CH₂— | CH₃ | CH₃ | | |
| 218 | C₆H₅ | —(CH₂)₅— | CH₃ | CH₃ | | |
| 219 | 2-Cl—C₆H₄ | —(CH₂)₅— | CH₃ | CH₃ | | |
| 220 | 4-Cl—C₆H₄ | —(CH₂)₅— | CH₃ | CH₃ | | |
| 221 | 2-Cl—C₆H₄ | —(CH₂)₅— | CH₃ | CH₃ | | |
| 222 | 4-Cl—C₆H₄ | —(CH₂)₅— | CH₃ | CH₃ | | |
| 223 | 2-OCH₃—C₆H₄ | —(CH₂)₅— | CH₃ | CH₃ | | |
| 224 | 4-OCH₃—C₆H₄ | —(CH₂)₅— | CH₃ | CH₃ | | |
| 225 | 4-CF₃—C₆H₄ | —(CH₂)₅— | CH₃ | CH₃ | | |
| 226 | C₆H₅ | —CH₂—CH₂—CH₂—CH(CH₃)—CH₂— | CH₃ | CH₃ | | |
| 227 | 2-CH₃—C₆H₄ | —CH₂—CH(CH₃)—CH₂—CH(CH₃)—CH₂— | CH₃ | CH₃ | | |
| 228 | 4-t-C₄H₉—C₆H₄ | —CH₂—CH(CH₃)—CH₂—CH(CH₃)—CH₂— | CH₃ | CH₃ | | |
| 229 | C₆H₅ | —(CH₂)₆— | CH₃ | CH₃ | | |
| 230 | C₆H₅ | —(CH₂)₄—CH(CH₃)—CH₂— | CH₃ | CH₃ | | |
| 231 | C₆H₅—O— | —CH₂— | CH₃ | CH₃ | | |
| 232 | 2-Cl—C₆H₄—O— | —CH₂— | CH₃ | CH₃ | | |
| 233 | 3-Cl—C₆H₄—O— | —CH₂— | CH₃ | CH₃ | | |
| 234 | 4-Cl—C₆H₄—O— | —CH₂— | CH₃ | CH₃ | | |
| 235 | 2,4-Cl₂—C₆H₃—O— | —CH₂— | CH₃ | CH₃ | | |

TABLE 1-continued $$R^3-(X)_n-\overset{O}{\underset{\|}{C}}-O-CH_2 \text{ (on benzene ring with } \overset{OR^2}{\underset{R^1OOC}{C=N}})$$

| No. | R³ | (X)ₙ | R² | R¹ | mp (°C.) | IR (cm⁻¹) |
|---|---|---|---|---|---|---|
| 236 | 2-CH₃—C₆H₄—O— | —CH₂— | CH₃ | CH₃ | | |
| 237 | 4-CH₃—C₆H₄—O— | —CH₂— | CH₃ | CH₃ | | |
| 238 | 2-OCH₃—C₆H₄—O— | —CH₂— | CH₃ | CH₃ | | |
| 239 | 4-OCH₃—C₆H₄—O— | —CH₂— | CH₃ | CH₃ | | |
| 240 | 4-CF₃—C₆H₄—O— | —CH₂— | CH₃ | CH₃ | | |
| 241 | C₆H₅—O— | —CH(CH₃)— | CH₃ | CH₃ | | |
| 242 | C₆H₅—O— | —CH₂—CH₂— | CH₃ | CH₃ | | |
| 243 | 2-Cl—C₆H₄—O— | —CH₂—CH₂— | CH₃ | CH₃ | | |
| 244 | 4-Cl—C₆H₄—O— | —CH₂—CH₂— | CH₃ | CH₃ | | |
| 245 | 2-CH₃—C₆H₄—O— | —CH₂—CH₂— | CH₃ | CH₃ | | |
| 246 | 4-CH₃—C₆H₄—O— | —CH₂—CH₂— | CH₃ | CH₃ | | |
| 247 | 2-OCH₃—C₆H₄—O— | —CH₂—CH₂— | CH₃ | CH₃ | | |
| 248 | 4-OCH₃—C₆H₄—O— | —CH₂—CH₂— | CH₃ | CH₃ | | |
| 249 | 4-t-C₄H₉—C₆H₄—O— | —CH₂—CH₂— | CH₃ | CH₃ | | |
| 250 | 4-sec.-C₄H₉—C₆H₄—O— | —CH₂—CH₂— | CH₃ | CH₃ | | |
| 251 | C₆H₅—O— | —(CH₂)₃— | CH₃ | CH₃ | | |
| 252 | 2-Cl—C₆H₄—O— | —(CH₂)₃— | CH₃ | CH₃ | | |
| 253 | 4-Cl—C₆H₄—O— | —(CH₂)₃— | CH₃ | CH₃ | | |
| 254 | 3-F—C₆H₄—O— | —(CH₂)₃— | CH₃ | CH₃ | | |
| 255 | 4-F—C₆H₄—O— | —(CH₂)₃— | CH₃ | CH₃ | | |
| 256 | 2-CH₃—C₆H₄—O— | —(CH₂)₃— | CH₃ | CH₃ | | |
| 257 | 4-CH₃—C₆H₄—O— | —(CH₂)₃— | CH₃ | CH₃ | | |
| 258 | 2-OCH₃—C₆H₄—O— | —(CH₂)₃— | CH₃ | CH₃ | | |
| 259 | 4-OCH₃—C₆H₄—O— | —(CH₂)₃— | CH₃ | CH₃ | | |
| 260 | 2,4-Cl₂—C₆H₃—O— | —(CH₂)₃— | CH₃ | CH₃ | | |
| 261 | 4-Cl—C₆H₄—O— | —CH(CH₃)—CH₂—CH₂— | CH₃ | CH₃ | | |
| 262 | 2-CF₃—C₆H₄—O— | —(CH₂)₃— | CH₃ | CH₃ | | |
| 263 | 3-CF₃—C₆H₄—O— | —(CH₂)₃— | CH₃ | CH₃ | | |
| 264 | 4-CF₃—C₆H₄—O— | —(CH₂)₃— | CH₃ | CH₃ | | |
| 265 | 4-t-butoxy-C₆H₄—O— | —(CH₂)₃— | CH₃ | CH₃ | | |
| 266 | 2-CH₃,4-Cl—C₆H₃—O— | —(CH₂)₃— | CH₃ | CH₃ | | |
| 267 | 2-C₂H₅—C₆H₄—O— | —(CH₂)₃— | CH₃ | CH₃ | | |
| 268 | 4-iso-C₃H₇—C₆H₄—O— | —(CH₂)₃— | CH₃ | CH₃ | | |
| 269 | 4-t-C₄H₉—C₆H₄—O— | —(CH₂)₃— | CH₃ | CH₃ | | |
| 270 | C₆H₅—O— | —CH₂—CH(CH₃)—CH₂— | CH₃ | CH₃ | | |
| 271 | C₆H₅—O— | —(CH₂)₄— | CH₃ | CH₃ | | |
| 272 | 2-Cl—C₆H₄—O— | —(CH₂)₄— | CH₃ | CH₃ | | |
| 273 | 4-Cl—C₆H₄—O— | —(CH₂)₄— | CH₃ | CH₃ | | |
| 274 | 2,4-Cl₂—C₆H₃—O— | —(CH₂)₄— | CH₃ | CH₃ | | |
| 275 | 2,6-Cl₂—C₆H₃—O— | —(CH₂)₄— | CH₃ | CH₃ | | |
| 276 | 2-CH₃—C₆H₄—O— | —(CH₂)₄— | CH₃ | CH₃ | | |
| 277 | 4-CH₃—C₆H₄—O— | —(CH₂)₄— | CH₃ | CH₃ | | |

TABLE 1-continued $$R^3-(X)_n-\overset{O}{\underset{\|}{C}}-O-CH_2 \underset{}{\overset{}{\diagup}} \overset{}{\underset{R^1OOC}{C}}=N \diagdown OR^2$$

| No. | R³ | (X)ₙ | R² | R¹ | mp (°C.) | IR (cm⁻¹) |
|---|---|---|---|---|---|---|
| 278 | C₆H₅—O— | —CH₂—CH₂—CH(CH₃)—CH₂— | CH₃ | CH₃ | | |
| 279 | C₆H₅—O— | —(CH₂)₅— | CH₃ | CH₃ | | |
| 280 | 3-Cl—C₆H₄—O— | —(CH₂)₅— | CH₃ | CH₃ | | |
| 281 | C₆H₅—O— | —(CH₂)₃—CH(CH₃)—CH₂— | CH₃ | CH₃ | | |
| 282 | C₆H₅—O— | —(CH₂)₆— | CH₃ | CH₃ | | |
| 283 | 3-Cl—C₆H₄—O— | —(CH₂)₆— | CH₃ | CH₃ | | |
| 284 | C₆H₅—O— | —(CH₂)₄—CH(CH₃)—CH₂— | CH₃ | CH₃ | | |
| 285 | A 1* | — | CH₃ | CH₃ | | |
| 286 | A 2* | — | CH₃ | CH₃ | | |
| 287 | A 3* | — | CH₃ | CH₃ | | |
| 288 | A 4* | — | CH₃ | CH₃ | | |
| 289 | A 5* | — | CH₃ | CH₃ | | |
| 290 | A 6* | — | CH₃ | CH₃ | | |
| 291 | A 7* | — | CH₃ | CH₃ | | |
| 292 | A 8* | — | CH₃ | CH₃ | | |
| 293 | A 9* | — | CH₃ | CH₃ | | |
| 294 | A 10* | — | CH₃ | CH₃ | | |
| 295 | A 11* | — | CH₃ | CH₃ | | |
| 296 | A 12* | — | CH₃ | CH₃ | 116-119 | 2950, 1728, 1295, 1169, 1069, 1020 |
| 297 | A 13* | — | CH₃ | CH₃ | 103-106 | 2950, 1720, 1284, 1222, 1168, 1091, 1074, 1015, 756 |
| 298 | A 14* | — | CH₃ | CH₃ | | |
| 299 | A 15* | — | CH₃ | CH₃ | | |
| 300 | A 16* | — | CH₃ | CH₃ | oil | 2970, 1743, 1275, 1222, 1069, 1019, 729 |
| 301 | A 17* | — | CH₃ | CH₃ | | |
| 302 | N-pyrrolyl | —CH(iso-C₃H₇)— | CH₃ | CH₃ | | |
| 303 | 4-tert.-butyl-C₆H₄ | —CH₂—C(CH₃)=CH—CH=CH— | CH₃ | CH₃ | | |
| 304 | H | —CH₂—CH(CH₃)—CH₂—CH(CH₃)— | CH₃ | CH₃ | | |
| 305 | H | —CH₂—CH(CH₃)—CH₂—CH(C₂H₅)— | CH₃ | CH₃ | | |
| 306 | H | —CH₂—CH(CH₃)—CH₂—CH(n-C₃H₇)— | CH₃ | CH₃ | | |
| 307 | H | —CH₂—CH(CH₃)—CH₂—CH(i-C₃H₇)— | CH₃ | CH₃ | | |
| 308 | H | —CH₂—C(CH₃)₂—CH₂—CH(CH₃)—CH₂— | CH₃ | CH₃ | | |
| 309 | H | —(CH₂)₅—CH(C₂H₅)— | CH₃ | CH₃ | | |
| 310 | H | —(CH₂)₅—CH(n-C₃H₇)— | CH₃ | CH₃ | oil | 2957, 1731, 1220, 1145, |
| 311 | H | —(CH₂)₄—O—CH₂—C(CH₃)₂— | CH₃ | CH₃ | | |

TABLE 1-continued $$R^3-(X)_n-\overset{O}{\underset{}{C}}-O-CH_2 \underset{R^1OOC}{\overset{}{\diagdown}} \overset{}{\underset{N}{\diagup}} \overset{OR^2}{}$$

(structure: 2-substituted phenyl with $R^1OOC-C(=N-OR^2)-$ and $-CH_2-O-C(=O)-(X)_n-R^3$ substituent)

| No. | R³ | (X)ₙ | R² | R¹ | mp (°C.) | IR (cm⁻¹) |
|---|---|---|---|---|---|---|
| 312 | H | —CH₂—O—CH₂—C(CH₃)₂— | CH₃ | CH₃ | oil | 1069,1020 2950, 1730, 1222, 1145, 1109, 1069, 1019 |
| 313 | C₆H₅ | —CH=CH—(CH₂)₄— | CH₃ | CH₃ | | |
| 314 | H | —CH₂—C(CH₃)₂—CH₂—CH(CH₃)₂—CH₂— | CH₃ | CH₃ | | |
| 315 | H | —CH₂—CH(CH₃)—(CH₂)₂—CH(i-C₃H₇)— | CH₃ | CH₃ | | |
| 316 | 1-methylcyclopropyl | — | CH₃ | CH₃ | 94-96 | 2980, 1739, 1714, 1302, 1171, 1069, 1011, 771. |
| 317 | 2-methylcyclopropyl | — | CH₃ | CH₃ | | |
| 318 | 2-phenylcyclopropyl | — | CH₃ | CH₃ | | |
| 319 | 1-methylcyclohexyl | — | CH₃ | CH₃ | | |
| 320 | 4-Cl—C₆H₄ | —CHCl— | CH₃ | CH₃ | | |
| 321 | 1-methylcyclopropyl | — | CH₃ | CH₃ | | |
| 322 | 1-methylcyclopropyl | — | CH₃ | i-C₃H₇ | | |
| 323 | 1-methylcyclopropyl | — | CH₃ | n-C₄H₉ | | |
| 324 | 1-methylcyclopropyl | — | CH₃ | n-C₅H₁₁ | | |
| 325 | 1-methylcyclopropyl | — | H | CH₃ | | |
| 326 | 1-methylcyclopropyl | — | C₂H₅ | CH₃ | | |
| 327 | 1-methylcyclopropyl | — | n-C₃H₇ | CH₃ | | |
| 328 | 1-methylcyclopropyl | — | n-C₄H₉ | CH₃ | | |
| 329 | 1-methylcyclopropyl | — | n-C₅H₁₁ | CH₃ | | |
| 330 | 1-methylcyclopropyl | — | CH₃ | CH₃ | | |
| 331 | 2-pyridyl | — | CH₃ | CH₃ | 123-126 | |
| 332 | 4-methyl-2-pyridyl | — | CH₃ | CH₃ | | |
| 333 | 4-fluoro-2-pyridyl | — | CH₃ | CH₃ | | |
| 334 | 4-chloro-2-pyridyl | — | CH₃ | CH₃ | | |
| 335 | 6-methyl-2-pyridyl | — | CH₃ | CH₃ | | |
| 336 | 6-ethyl-2-pyridyl | — | CH₃ | CH₃ | | |
| 337 | 6-n-propyl-2-pyridyl | — | CH₃ | CH₃ | | |
| 338 | 6-iso-propyl-2-pyridyl | — | CH₃ | CH₃ | | |
| 339 | 6-n-butyl-2-pyridyl | — | CH₃ | CH₃ | | |
| 340 | 6-chloro-2-pyridyl | — | CH₃ | CH₃ | | |
| 341 | 3,6-dichloro-2-pyridyl | — | CH₃ | CH₃ | | |
| 342 | 5-n-butyl-2-pyridyl | — | CH₃ | CH₃ | | |
| 343 | 3-pyridyl | — | CH₃ | CH₃ | | |
| 344 | 2-methyl-3-pyridyl | — | CH₃ | CH₃ | | |
| 345 | 2-chloro-3-pyridyl | — | CH₃ | CH₃ | | |
| 346 | 2-fluoro-3-pyridyl | — | CH₃ | CH₃ | | |

TABLE 1-continued

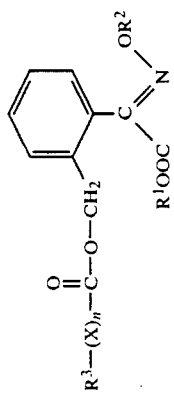

| No. | R³ | (X)ₙ | R² | R¹ | mp (°C) | IR (cm⁻¹) |
|---|---|---|---|---|---|---|
| 347 | 4-chloro-3-pyridyl | — | CH₃ | CH₃ | | |
| 348 | 5-fluoro-3-pyridyl | — | CH₃ | CH₃ | | |
| 349 | 6-chloro-3-pyridyl | — | CH₃ | CH₃ | | |
| 350 | 4-pyridyl | — | CH₃ | CH₃ | | |
| 351 | 2-methyl-4-pyridyl | — | CH₃ | CH₃ | | |
| 352 | 2,6-dimethyl-4-pyridyl | — | CH₃ | CH₃ | | |
| 353 | 2,3-dimethyl-4-pyridyl | — | CH₃ | CH₃ | | |
| 354 | 2-phenyl-3-methyl-4-pyridyl | — | CH₃ | CH₃ | | |
| 355 | 3-methyl-4-pyridyl | — | CH₃ | CH₃ | | |
| 356 | 2-ethyl-4-pyridyl | — | CH₃ | CH₃ | | |
| 357 | 2-n-propyl-4-pyridyl | — | CH₃ | CH₃ | | |
| 358 | 2-n-butyl-4-pyridyl | — | CH₃ | CH₃ | | |
| 359 | 2-chloro-4-pyridyl | — | CH₃ | CH₃ | | |
| 360 | 2,6-dichloro-4-pyridyl | — | CH₃ | CH₃ | | |
| 361 | 2-quinolyl | — | CH₃ | CH₃ | | |
| 362 | 3-quinolyl | — | CH₃ | CH₃ | | |
| 363 | 4-quinolyl | — | CH₃ | CH₃ | | |
| 364 | 2-methyl-4-quinolyl | — | CH₃ | CH₃ | | |
| 365 | 2-ethyl-4-quinolyl | — | CH₃ | CH₃ | | |
| 366 | 2-n-propyl-4-quinolyl | — | CH₃ | CH₃ | | |
| 367 | 2-iso-propyl-4-quinolyl | — | CH₃ | CH₃ | | |
| 368 | 2-tert-butyl-4-quinolyl | — | CH₃ | CH₃ | | |
| 369 | 2-cyclohexyl-4-quinolyl | — | CH₃ | CH₃ | | |
| 370 | 3-methyl-4-quinolyl | — | CH₃ | CH₃ | | |
| 371 | 3-ethyl-4-quinolyl | — | CH₃ | CH₃ | | |
| 372 | 3-n-propyl-4-quinolyl | — | CH₃ | CH₃ | | |
| 373 | 3-n-butyl-4-quinolyl | — | CH₃ | CH₃ | | |
| 374 | 3-phenyl-4-quinolyl | — | CH₃ | CH₃ | | |
| 375 | 3-benzyl-4-quinolyl | — | CH₃ | CH₃ | | |
| 376 | 2-methyl-3-acetyl-4-quinolyl | — | CH₃ | CH₃ | | |
| 377 | 2-phenyl-3-methoxy-4-quinolyl | — | CH₃ | CH₃ | | |
| 378 | 2-methyl-3-cyano-4-quinolyl | — | CH₃ | CH₃ | | |
| 379 | 6-methyl-4-quinolyl | — | CH₃ | CH₃ | | |
| 380 | 6-chloro-4-quinolyl | — | CH₃ | CH₃ | | |
| 381 | 7-chloro-4-quinolyl | — | CH₃ | CH₃ | | |
| 382 | 7-chloro-8-methyl-3-quinolyl | — | CH₃ | CH₃ | | |
| 383 | 2,2-dichlorocyclopropyl | — | CH₃ | CH₃ | | |
| 384 | 2-furyl | —CH=CH— | CH₃ | CH₃ | 58–60 | |
| 385 | 1-phenylcyclopropyl | — | CH₃ | CH₃ | | |
| 386 | 1-(2'methylphenyl)-cyclopropyl | — | CH₃ | CH₃ | | |
| 387 | 1-(3'-methylphenyl)-cyclopropyl | — | CH₃ | CH₃ | | |
| 388 | 1-(4'-methylphenyl)-cyclopropyl | — | CH₃ | CH₃ | | |

TABLE 1-continued

Structure:

R³—(X)ₙ—C(=O)—O—CH₂—[phenyl]—C(=N—OR²)—COOR¹

| No. | R³ | (X)ₙ | R² | R¹ | mp (°C.) | IR (cm⁻¹) |
|---|---|---|---|---|---|---|
| 389 | 1-(3',4'-dimethylphenyl)-cyclopropyl | — | CH₃ | CH₃ | | |
| 390 | 1-(4'-tert.butylphenyl)-cyclopropyl | — | CH₃ | CH₃ | | |
| 391 | 1-(3'-trifluoromethylphenyl)-cyclopropyl | — | CH₃ | CH₃ | | |
| 392 | 1-(2'-fluorophenyl)-cyclopropyl | — | CH₃ | CH₃ | | |
| 393 | 1-(3'-fluorophenyl)-cyclopropyl | — | CH₃ | CH₃ | | |
| 394 | 1-(4'-fluorophenyl)-cyclopropyl | — | CH₃ | CH₃ | | |
| 395 | 1-(2'-chlorophenyl)-cyclopropyl | — | CH₃ | CH₃ | | |
| 396 | 1-(3'-chlorophenyl)-cyclopropyl | — | CH₃ | CH₃ | | |
| 397 | 1-(2',6'dichlorophenyl)-cyclopropyl | — | CH₃ | CH₃ | | |
| 398 | 1-(3',4'-dichlorophenyl)-cyclopropyl | — | CH₃ | CH₃ | | |
| 399 | 1-(4'-bromophenyl)-cyclopropyl | — | CH₃ | CH₃ | | |
| 400 | 1-(2'-methoxyphenyl)-cyclopropyl | — | CH₃ | CH₃ | | |
| 401 | 1-(3'-methoxyphenyl)-cyclopropyl | — | CH₃ | CH₃ | | |
| 402 | 1-(4'-methoxyphenyl)-cyclopropyl | — | CH₃ | CH₃ | | |
| 403 | 1-(2',4'-dimethoxyphenyl)-cyclopropyl | — | CH₃ | CH₃ | | |
| 404 | 1-(2',6'-dimethoxyphenyl)-cyclopropyl | — | CH₃ | CH₃ | | |
| 405 | 1-(3',4'-dimethoxyphenyl)-cyclopropyl | — | CH₃ | CH₃ | | |
| 406 | 1-(3',4'-diethoxyphenyl)-cyclopropyl | — | CH₃ | CH₃ | | |
| 407 | 1-trifluoromethylcyclopropyl | — | CH₃ | CH₃ | 68 | 2970, 1746, 1724, 1404, 1145, 1110, 1012 |
| 408 | 1-trimethylsilylcyclopropyl | — | CH₃ | CH₃ | 68 | 2950, 1719, 1713, 1273, 1153, 1067, 1017, 837 |
| 409 | 2-furyl | — | CH₃ | CH₃ | 82–84 | |
| 410 | 2-thiophenyl | — | CH₃ | CH₃ | 88–90 | |
| 411 | 2-thiophenyl | —CH=CH— | CH₃ | CH₃ | 60 | |
| 412 | 2,6-(OCH₃)₂—C₆H₃ | — | CH₃ | CH₃ | oil | 2950, 1733, 1597, 1476, 1257, 1113, 1069, 1018 |
| 413 | 2-F, 6-Cl—C₆H₃ | — | CH₃ | CH₃ | oil | 2950, 1738, 1450, 1270, 1069, 1019, 902, 791 |
| 414 | 2-(N-methyl)-pyrrolyl | — | CH₃ | CH₃ | oil | 2960, 1726, 1705, 1412, 1322, 1244, 1104, 1069, 1018 |
| 415 | N-pyrazolyl | —CH(iso-C₃H₇)— | CH₃ | CH₃ | oil | 2970, 1743, 1394, 1279, 1222, 1069, 1019, 754 |
| 416 | 1,2,4-triazol-1-yl | —CH(iso-C₃H₇)— | CH₃ | CH₃ | oil | 2970, 1743, 1438, 1276, 1222, 1069, 1017, 957 |

TABLE 1-continued

Structure:
$R^3-(X)_n-\overset{O}{\underset{\|}{C}}-O-CH_2-$ attached to phenyl ring with $\underset{R^1OOC}{C}=N-OR^2$ substituent

| No. | $R^3$ | $(X)_n$ | $R^2$ | $R^1$ | mp (°C.) | IR (cm$^{-1}$) |
|---|---|---|---|---|---|---|
| 417 | 1-naphthyl | — | $CH_3$ | $CH_3$ | oil | 2950, 1723, 1242, 1196, 1132, 1069, 1017, 784 |
| 418 | 9-anthracenyl | — | $CH_3$ | $CH_3$ | oil | 2950, 1725, 1199, 1069, 1016, 734 |
| 419 | 1-(4'-chlorophenyl)-cyclobutyl | —$CH_2$— | $CH_3$ | $CH_3$ | — | |
| 420 | 3-$CF_3$—$C_6H_4$ | —$CH_2$— | $CH_3$ | $CH_3$ | oil | 2950, 1738, 1439, 1331, 1168, 1125, 1072, 1022 |
| 421 | 3,4-$(OC_2H_5)_2$—$C_6H_3$ | —$CH_2$— | $CH_3$ | $CH_3$ | oil | 2980, 1738, 1514, 1261, 1223, 1142, 1069, 1019 |
| 422 | 3,4,5-$(OCH_3)_3$—$C_6H_2$ | —$C(CH_3)_2$—$CH_2$— | $CH_3$ | $CH_3$ | oil | 2940, 1733, 1591, 1461, 1319, 1223, 1127, 1069, 1017 |
| 423 | 4-F—$C_6H_4$ | —$C(CH_3)_2$—$CH(CH_3)$— | $CH_3$ | $CH_3$ | oil | 2980, 1731, 1512, 1322, 1223, 1069, 1019, 835 |
| 424 | 4-F—$C_6H_4$ | — | $CH_3$ | $CH_3$ | oil | 2980, 1731, 1511, 1223, 1069, 1019, 836 |
| 425 | 2-$CH_3$, 6-$NO_2$—$C_6H_3$ | — | $CH_3$ | $CH_3$ | 87–89 | 2950, 1741, 1531, 1344, 1270, 1067, 758 |

*) For formulae, see above text

Generally speaking, the novel compounds are extremely effective on a broad spectrum of phytopathogenic fungi, in particular those from the Ascomycetes and Basidiomycetes classes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:

*Erysiphe graminis* in cereals,
*Erysiphe cichoracearum* and *Sphaerotheca fuliginea* in cucurbits,
*Podosphaera leucotricha* in apples,
*Uncinula necator* in vines,
Puccinia species in cereals,
Rhizoctonia species in cotton and lawns,
Ustilago species in cereals and sugar cane,
*Venturia inaequalis* (scab) in apples,
Helminthosporium species in cereals,
*Septoria nodorum* in wheat,
*Botrytis cinerea* (gray mold) in strawberries and grapes,
*Cercospora arachidicola* in groundnuts,
*Pseudocercosporella herpotrichoides* in wheat and barley,
*Pyricularia oryzae* in rice,
*Phytophthora infestans* in potatoes and tomatoes,
Fusarium and Verticillium species in various plants,
*Plasmopara viticola* in grapes,
Alternaria species in fruit and vegetables.

The compounds are applied by spraying or dusting the plants with the active ingredients, or treating the seeds of the plants with the active ingredients. They may be applied before or after infection of the plants or seeds by the fungi.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin, sulfite waste liquors and methylcellulose.

The fungicidal agents generally contain from 0.1 to 95, and preferably from 0.5 to 90, wt % of active ingredient. The application rates are from 0.02 to 3 kg or more of active ingredient per hectare, depending on the type of effect desired. The novel compounds may also be used for protecting materials, for example against Paecilomyces variotii.

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. 90 parts by weight of compound no. 316 is mixed with 10 parts by weight of N-methyl-α-pyrrolidone. A mixture is obtained which is suitable for application in the form of very fine drops.

II. 20 parts by weight of compound no. 316 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 316 is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 316 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 316 is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 316 is intimately mixed with 97 parts by weight of particulate kaolin. A dust is obtained containing 3% by weight of the active ingredient.

VII. 30 parts by weight of compound no. 316 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 316 is intimately mixed with 10 parts by weight of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts by weight of compound no. 316 is intimately mixed with 2 parts by weight of the calcium salt of dodecylbenzenesulfonic acid, 8 parts by weight of a fatty alcohol polyglycol ether, 2 parts by weight of the sodium salt of a phenolsulfonic acidurea-formaldehyde condensate and 68 parts by weight of a paraffinic mineral oil. A stable oily dispersion is obtained.

In these application forms, the agents according to the invention may also be present together with other active ingredients, for example herbicides, insecticides, growth regulators, and fungicides, and may furthermore be mixed and applied together with fertilizers. Admixture with other fungicides frequently results in an increase in the fungicidal spectrum.

The following list of fungicides with which the novel compounds may be combined is intended to illustrate possible combinations but not to impose any restrictions. Examples of fungicides which may be combined with the novel compounds are:

sulfur,
dithiocarbamates and their derivatives, such as
ferric dimethyldithiocarbamate,
zinc dimethyldithiocarbamate,
zinc ethylenebisdithiocarbamate,
manganese ethylenebisdithiocarbamate,
manganese zinc ethylenediaminebisdithiocarbamate,
tetramethylthiuram disulfides,
ammonia complex of zinc N,N'-ethylenebisdithiocarbamate,
ammonia complex of zinc N,N'-propylenebisdithiocarbamate,
zinc N,N'-propylenebisdithiocarbamate and N,N'-polypropylenebis(thiocarbamyl) disulfide;
nitro derivatives, such as
dinitro(1-methylheptyl)-phenyl crotonate,
2-sec-butyl-4,6-dinitrophenyl 3,3-dimethylacrylate,
2-sec-butyl-4,6-dinitrophenyl isopropylcarbonate and diisopropyl 5-nitroisophthalate;
heterocyclic substances, such as
2-heptadecylimidazol-2-yl acetate,
2,4-dichloro-6-(o-chloroanilino)-s-triazine,
0,0-diethyl phthalimidophosphonothioate,
5-amino-1-[-bis-(dimethylamino)-phosphinyl]-3-phenyl-1,2,4-triazole,
2,3-dicyano-1,4-dithioanthraquinone,
2-thio-1,3-dithio[4,5-b]quinoxaline,
methyl 1-(butylcarbamyl)-2-benzimidazolecarbamate,
2-methoxycarbonylaminobenzimidazole,
2-(fur-2-yl)-benzimidazole,
2-(thiazol-4-yl)benzimidazole,
N-(1,1,2,2-tetrachloroethylthio)-tetrahydrophthalimide,
N-trichloromethylthiotetrahydrophthalimide,
N-trichloromethylthiophthalimide,
N-dichlorofluoromethylthio-N',N'-dimethyl-N-phenylsulfuric acid diamide,
5-ethoxy-3-trichloromethyl-1,2,3-thiadiazole,
2-thiocyanatomethylthiobenzothiazole,
1,4-dichloro-2,5-dimethoxybenzene,
4-(2-chlorophenylhydrazono)-3-methyl-5-isoxazolone,
2-thiopyridine 1-oxide,
8-hydroxyquinoline and its copper salt,
2,3-dihydro-5-carboxanilido-6-methyl-1,4-oxathiyne,
2,3-dihydro-5-carboxanilido-6-methyl-1,4-oxathiyne 4,4-dioxide,
2-methylfuran-3-carboxanilide,
2,5-dimethylfuran-3-carboxanilide,
2,4,5-trimethylfuran-3-carboxanilide,
2,5-dimethyl-N-cyclohexylfuran-3-carboxamide,
N-cyclohexyl-N-methoxy-2,5-diethylfuran-3-carboxamide,
2-methylbenzanilide,
2-iodobenzanilide,
N-formyl-N-morpholine-2,2,2-trichloroethylacetal,
piperazine-1,4-diylbis-(1-(2,2,2-trichloroethyl)-formamide),
1-(3,4-dichloroanilino)-1-formylamino-2,2,2-trichloroethane,
2,6-dimethyl-N-tridecylmorpholine and its salts,
2,6-dimethyl-N-cyclododecylmorpholine and its salts,
N-[3-(p-tert.-butylphenyl)-2-methylpropyl]-cis-2,6-dimethylmorpholine,
N-[3-(p-tert.-butylphenyl)-2-methylpropyl]-piperidine,
1-[2-(2,4-dichlorophenyl)-4-ethyl-1,3-dioxolan-2-ylethyl]-1H-1,2,4-triazole,
1-[2-(2,4-dichlorophenyl)-4-n-propyl-1,3-dioxolan-2-ylethyl]-1H-1,2,4-triazole,
N-(n-propyl)-N-(2,4,6-trichlorophenoxyethyl)-N'-imidazolyl-urea,
1-(4-chlorophenoxy)-3,3-dimethyl-1-(1H-1,2,4-triazol-1-yl)-butan-2-one,
1-(4-chlorophenoxy)-3,3-dimethyl-1-(1H-1,2,4-triazol-1-yl)-butan-2-ol,
1-(4-phenylphenoxy)-3,3-dimethyl-1-(1H-1,2,4-triazol-1-yl)-2-butanol,
α-(2-chlorophenyl)-α-(4-chlorophenyl)-5-pyrimidinemethanol,
5-butyl-(2-dimethylamino-4-hydroxy-6-methylpyrimidine,
bis-(p-chlorophenyl)-3-pyridinemethanol,
1,2-bis-(3-ethoxycarbonyl-2-thioureido)-benzene,
1,2-bis-(3-methoxycarbonyl-2-thioureido)-benzene,
and various fungicides, such as
dodecylguanidine acetate,
3-[3-(3,5-dimethyl-2-oxycyclohexyl)-2-hydroxyethyl]-glutaramide, hexachlorobenzene,
DL-methyl-N-(2,6-dimethylphenyl)-N-fur-2-yl alanate,
methyl DL-N-(2,6-dimethylphenyl)-N-(2'-methoxyacetyl)-alanate,
N-(2,6-dimethylphenyl)-N-chloroacetyl-DL-2-aminobutyrolactone,
methyl DL-N-(2,6-dimethylphenyl)-N-(phenylacetyl)-alanate,
5-methyl-5-vinyl-3-(3,5-dichlorophenyl)-2,4-dioxo-1,3-oxazolidine,
3-[3,5-dichlorophenyl]-5-methyl-5-methoxymethyl-1,3-oxazolidine-2,4-dione,
3-(3,5-dichlorophenyl)-1-isopropylcarbamylhydantoin,
N-(3,5-dichlorophenyl)-1,2-dimethylcyclopropane-1,2-dicarboximide,
2-cyano-[N-(ethylaminocarbonyl)-2-methoximino]-acetamide,
1-[2-(2,4-dichlorophenyl)-pentyl]-1H-1,2,4-triazole,
2,4-difluoro-α-(1H-1,2,4-triazol-1-ylmethyl)-benzhydryl alcohol,
N-(3-chloro-2,6-dinitro-4-trifluoromethylphenyl)-5-trifluoromethyl-3-chloro-2-aminopyridine, and
1-((bis-(4-fluorophenyl)-methylsilyl)-methyl)-1H-1,2,4-triazole.

USE EXAMPLES

The active ingredient 2-benzyloxyphenylglyoxylic acid methyl ester-0-methyl oxime (A) disclosed in EP 253,213 was used for comparison purposes.

USE EXAMPLE 1

Action on *Pyrenophora teres*

Barley seedlings of the "Igri" variety were sprayed to runoff at the two-leaf stage with aqueous suspensions consisting (dry basis) of 80% of active ingredient and 20% of emulsifier. After 24 hours the plants were inoculated with a spore suspension of the fungus *Pyrenophora teres*, and set up for 48 hours in a high-humidity climatic cabinet at 18° C. The plants were then cultivated for a further 5 days in the greenhouse at 20° to 22° C. and a relative humidity of 70° C. The extent of fungus spread was then assessed.

The results show that active ingredient 316, applied as a 0.05 wt % spray liquor, has a better fungicidal action (95%) than prior art comparative agent A (80%).

We claim:

1. A compound of the formula I

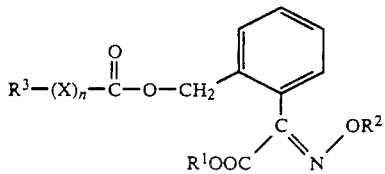

(I)

where
$R^1$ and $R^2$ are each hydrogen or $C_1$–$C_5$-alkyl,
$R^3$ is hydrogen, halogen, aryl or aryloxy, the aromatic ring being unsubstituted or substituted by $C_1$–$C_6$-alkyl, $C_2$–$C_4$-alkenyl, $C_1$–$C_2$-haloalkyl, $C_1$–$C_6$-alkoxy, $C_1$–$C_4$-alkoxy-$C_1$–$C_4$-alkyl, aryl, aryl-$C_1$–$C_2$-alkyl, aryloxy, aryloxy-$C_1$–$C_4$-alkyl, aryloxy-$C_1$–$C_4$-alkoxy, haloaryloxy-$C_1$–$C_4$-alkoxy, halogen, halogen-$C_1$–$C_4$-alkoxy, $C_1$–$C_4$-alkylthio or nitro, or $R^3$ is adamantyl, fluorenyl or $C_3$–$C_7$-cycloalkyl or $C_5$–$C_6$-cycloalkenyl, these radicals being unsubstituted or substituted by $C_1$–$C_4$-alkyl, halogen, $C_1$–$C_2$-haloalkyl, $C_3$–$C_4$-alkenyl, acetyl, $C_2$–$C_4$-haloalkenyl, methoxycarbonyl-$C_3$–$C_4$-alkenyl, phenyl, cyclopentylidenemethyl, halophenyl, $C_1$–$C_2$-alkoxyphenyl or $C_1$–$C_4$-alkylphenyl, wherein the aryl portion of aryl, aryloxy, arylalkyl, aryloxyalkyl, aryloxyalkoxy and haloaryloxyalkoxy is phenyl or naphthyl;
X is saturated or unsaturated $C_1$–$C_{12}$-alkylene which is unsubstituted or substituted by halogen or hydroxy, and
n is 0 or 1.

2. A process for combating fungi, wherein the fungi, or the materials, plants, seed or the soil to be protected against fungus attack are treated with a fungicidally effective amount of a compound of the formula I

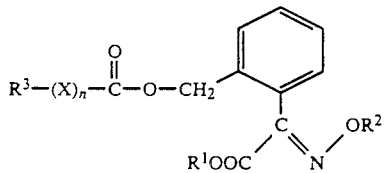

(I)

where
$R^1$ and $R^2$ are each hydrogen or $C_1$–$C_5$-alkyl,
$R^3$ is hydrogen, halogen, aryl or aryloxy, the aromatic ring being unsubstituted or substituted by $C_1$–$C_6$-alkyl, $C_2$–$C_4$-alkenyl, $C_1$–$C_2$-haloalkyl, $C_1$–$C_6$-alkoxy, $C_1$–$C_4$-alkoxy-$C_1$–$C_4$-alkyl, aryl, aryl-$C_1$–$C_2$-alkyl, aryloxy, aryloxy-$C_1$–$C_4$-alkyl, aryloxy-$C_1$–$C_4$-alkoxy, haloaryloxy $C_1$–$C_4$-alkoxy, halogen, halogen-$C_1$–$C_4$-alkoxy, $C_1$–$C_4$-alkylthio or nitro, or $R^3$ is adamantyl, fluorenyl or $C_3$–$C_7$-cycloalkyl or $C_5$–$C_6$-cycloalkenyl, these radicals being unsubstituted or substituted by $C_1$–$C_4$-alkyl, halogen, $C_1$–$C_2$-haloalkyl, $C_3$–$C_4$-alkenyl, acetyl, $C_2$–$C_4$-haloalkenyl, methoxycarbonyl-$C_3$–$C_4$-alkenyl, phenyl, cyclopentylidenemethyl, halophenyl, $C_1$–$C_2$-alkoxyphenyl or $C_1$–$C_4$-alkylphenyl, wherein the aryl portion of aryl, aryloxy, arylalkyl, aryloxyalkyl, aryloxyalkoxy and haloaryloxyalkoxy is phenyl or naphthyl;
X is saturated or unsaturated $C_1$–$C_{12}$-alkylene which is unsubstituted or substituted by halogen or hydroxy, and
n is 0 or 1.

3. A fungicide containing an inert carrier and a fungicidally effective amount of a compound of the formula I

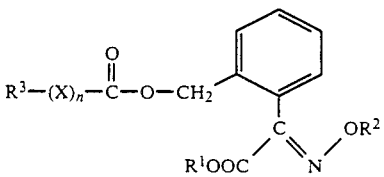

(I)

where
$R^1$ and $R^2$ are each hydrogen or $C_1$–$C_5$-alkyl,
$R^3$ is hydrogen, halogen, aryl or aryloxy, the aromatic ring being unsubstituted or substituted by $C_1$–$C_6$-alkyl, $C_2$–$C_4$-alkenyl, $C_1$–$C_2$-haloalkyl, $C_1$–$C_6$-alkoxy, $C_1$–$C_4$-alkoxy-$C_1$–$C_4$-alkyl, aryl, aryl-$C_1$–$C_2$-alkyl, aryloxy, aryloxy-$C_1$–$C_4$-alkyl, aryloxy-$C_1$–$C_4$-alkoxy, haloaryloxy $C_1$–$C_4$-alkoxy, halogen, halogen-$C_1$–$C_4$-alkoxy, $C_1$–$C_4$-alkylthio or nitro, or $R^3$ is adamantyl, fluorenyl or $C_3$–$C_7$-cycloalkyl or $C_5$–$C_6$-cycloalkenyl, these radicals being unsubstituted or substituted by $C_1$–$C_4$-alkyl, halogen, $C_1$–$C_2$-haloalkyl, $C_3$–$C_4$-alkenyl, acetyl, $C_2$–$C_4$-haloalkenyl, methoxycarbonyl-$C_3$–$C_4$-alkenyl, phenyl, cyclopentylidenemethyl, halophenyl, $C_1$–$C_2$-alkoxyphenyl or $C_1$–$C_4$-alkylphenyl, wherein the aryl portion of aryl, aryloxy, arylalkyl, aryloxyalkyl, aryloxyalkoxy and haloaryloxyalkoxy is phenyl or naphthyl;
X is saturated or unsaturated $C_1$–$C_{12}$-alkylene which is unsubstituted or substituted by halogen or hydroxy, and
n is 0 or 1.

4. A compound of the formula I as set forth in claim 1, where $R^1$ and $R^2$ are methyl, $R^3$ is 1-methylcyclopropyl and n is 0.

5. A compound of the formula I as set forth in claim 1, where $R^1$ and $R^2$ are methyl, $R^3$ is 1-(4-chlorophenyl)-cyclopropyl and n is 0.

6. A compound of the formula I as set forth in claim 1, where $R^1$ and $R^2$ are methyl, $R^3$ is 1-(2,4-dichlorophenyl)-cyclopropyl and n is 0.

* * * * *